(12) United States Patent
Bliss

(10) Patent No.: US 6,484,721 B1
(45) Date of Patent: Nov. 26, 2002

(54) PNEUMATIC OXYGEN CONSERVING DEVICE

(75) Inventor: Peter L. Bliss, Prior Lake, MN (US)

(73) Assignee: Chad Therapeutics, Inc., Chatsworth, CA (US)

( * ) Notice: Subject to any disclaimer, the term of this patent is extended or adjusted under 35 U.S.C. 154(b) by 0 days.

(21) Appl. No.: 09/893,178

(22) Filed: Jun. 27, 2001

(51) Int. Cl.[7] ................................................ A62B 9/02
(52) U.S. Cl. ............................ 128/205.24; 128/204.18; 128/207.18; 600/538
(58) Field of Search ....................... 128/200.24, 204.18, 128/204.21, 204.23, 204.26, 205.24, 207.14, 207.16, 207.18; 600/529, 533, 537, 538

(56) References Cited

U.S. PATENT DOCUMENTS

| | | | |
|---|---|---|---|
| 2,766,752 A | 10/1956 | Meidenbauer, Jr. | 123/142 |
| 4,345,592 A * | 8/1982 | Giorgini et al. | 128/204.26 |
| 4,449,524 A * | 5/1984 | Gray | 128/204.26 |
| 4,617,924 A * | 10/1986 | Heim et al. | 128/204.18 |
| 4,699,139 A * | 10/1987 | Marshall et al. | 128/207.18 |
| 5,360,000 A | 11/1994 | Carter | 128/204.26 |
| 5,464,009 A | 11/1995 | Tatarek-Gintowt | 128/205.24 |
| 5,487,383 A * | 1/1996 | Levinson | 128/205.24 |
| 5,664,562 A * | 9/1997 | Bourdon | 128/204.24 |
| 5,666,945 A | 9/1997 | Davenport | 128/200.14 |
| 5,671,730 A * | 9/1997 | Ollila | 128/200.24 |
| 5,848,975 A * | 12/1998 | Phillips | 600/529 |
| 5,881,725 A | 3/1999 | Hoffman et al. | 128/204.26 |
| 6,164,276 A * | 12/2000 | Bathe et al. | 128/205.24 |
| 6,176,235 B1 * | 1/2001 | Benarrouch et al. | 128/200.24 |

FOREIGN PATENT DOCUMENTS

WO    WO99/22795    5/1999 ................ 16/20

* cited by examiner

*Primary Examiner*—William E. Tapolcai
*Assistant Examiner*—Mohammad M Ali
(74) *Attorney, Agent, or Firm*—Nikolai & Mersereau, P.A.

(57) ABSTRACT

A pneumatic oxygen conserving device for efficiently dispensing oxygen or other gas used during respiratory therapy such that only the first part of the patient's breath contains the oxygen or other therapeutic gas. A gas delivery device is used which is triggered when the patient begins to inhale. A tail of gas flow is delivered to the patient after the initial inhalation timed period to prevent pulsing of gas delivery to the patient. In this manner gas is only delivered to the patient during the first portion of inhalation preventing gas from being delivered which will only fill the air passageways to the patient's lungs. By efficiently using the oxygen, cylinder bottles of oxygen used when a patient is mobile will last longer and be smaller and easier to transport. By pneumatically delivering the gas to the patient no batteries or electronics are used.

17 Claims, 2 Drawing Sheets

PNEUMATIC OXYGEN CONSERVING DEVICE

BACKGROUND OF THE INVENTION

I. Field of the Invention

This invention relates to respiratory gas delivery devices, which are responsive to a patient's breathing cycle and more particularly for providing oxygen to a patient only during the first portion of inhalation, such that oxygen is delivered to the patient only when it will be admitted to the lungs and not when it will remain in the patient's air passageways only to be exhaled.

II. Description of the Related Art

Patients with lung diseases frequently need oxygen delivered to their lungs as part of their therapy.

A continuous flow of oxygen to the patient is easily applied such that when the patient inhales there is oxygen available in a mask or cannula. However a continuous flow is not needed, particularly while the patient is exhaling.

Patient mobility is affected by the size of the oxygen bottles, their weight and how long they will last while the patient is carrying their oxygen supply with them. An oxygen economizing device can be used to make the oxygen in the bottle last longer and also reduce the size and weight of the bottle that needs to be transported with the patient for greater mobility.

Some oxygen economizers use electronic sensors and controls to deliver oxygen. This requires batteries, which must be constantly replaced and electronic controls, which may fail.

Some oxygen economizers use dual lumen cannulas, with one lumen for delivery of oxygen to the patient and one lumen for sensing breathing pressures. Dual lumen cannulas cost more and are not as comfortable for the patient.

Oxygen delivery devices have been developed wherein oxygen is supplied to the patient starting when the patient begins to inhale and ending when the patient begins to exhale, thus conserving oxygen. However, this too wastes oxygen as the patient only benefits from the first part of the oxygen inhaled, which goes to the patient's lungs. The remainder of the inhaled oxygen remains in the air passageways to the lungs and is immediately exhaled, thus wasting oxygen.

At least one oxygen economizer uses a series of pulses of oxygen during the inhalation cycle. The pulse of oxygen is delivered and then a check is made to see if the patient is still inhaling. If he is then another pulse is delivered. This method is irritating for the patient and wastes oxygen as the airways of the patient as well as the lungs receive oxygen.

A device is needed which will provide oxygen during initial inhalation and then reduce or eliminate the amount of oxygen delivered thereafter rather than deliver gas as a series of pulses. The oxygen delivery device should provide either a fixed or adjustable volume of oxygen for a fixed time at a fixed or adjustable flow rate such that patients having different breathing patterns can be treated. The oxygen delivery device should be pneumatic, avoiding batteries and other problems associated with electronic devices. The oxygen delivery device should also be used with a comfortable single lumen cannula.

SUMMARY OF THE INVENTION

The invention provides for a diaphragm to detect the commencement of inhalation and a timed application of oxygen such that the first portion of the inhalation in the breathing cycle receives oxygen and the balance of the inhalation cycle receives little or no oxygen.

The invention comprises a breath sensing portion with a sensing diaphragm for detecting a drop in pressure when a patient starts inhaling. The diaphragm moves to reduce the pressure in a gas delivery timer portion wherein a delivery diaphragm is displaced from a gas delivery seat for an adjustable amount of time to provide oxygen to a patient during the first portion of inhalation. The volume and flow rate of oxygen delivered to the patient is regulated by a variable flow rate portion in combination with the gas delivery timer portion. When oxygen begins flowing to the patient, oxygen entering the sensing chamber pushes the sensing diaphragm over a seat leading to the gas delivery timer portion. Oxygen entering the gas delivery timer portion builds up pressure and moves a diaphragm over a seat, cutting off the oxygen supply to the patient after the initial portion of inhalation. In this manner oxygen is delivered to the patient's lungs and not to his airways, which will be immediately expelled on exhaling.

If oxygen is only delivered during early inspiration, there will be a negative pressure in the cannula again at the end of the gas delivery. It is not desirable to deliver a second pulse, which would likely be only wasted. The invention avoids this phenomenon by providing a low flow "tail volume" from a reservoir which creates enough back pressure in the cannula to block out any continued patient effort.

OBJECTS OF THE INVENTION

It is an object of the invention to use oxygen efficiently during respiratory therapy.

It is an object of the invention to provide oxygen to a patient only during initial inspiration to avoid filling the airway of the patient with oxygen.

It is an object of the invention to use a pneumatic control device to deliver oxygen to the patient.

It is an object of the invention to provide a selectable preset volume of oxygen to the patient during each breath.

It is an object of the invention to extend the duration of use of each bottle of oxygen.

It is an object of the invention to reduce the size of the bottle of oxygen that a patient needs to transport when mobile.

It is an object of the invention to reduce the weight of the bottle of oxygen that a patient needs to transport when mobile.

It is an object of the invention to avoid multiple pulses of oxygen flowing to the patient.

It is an object of the invention to use a lumen single cannula with the pneumatic oxygen conserving device.

Other objects, advantages and novel features of the present invention will become apparent from the following detailed description of the invention when considered in conjunction with the accompanying drawing.

DESCRIPTION OF THE PREFERRED EMBODIMENTS

Figure 1:
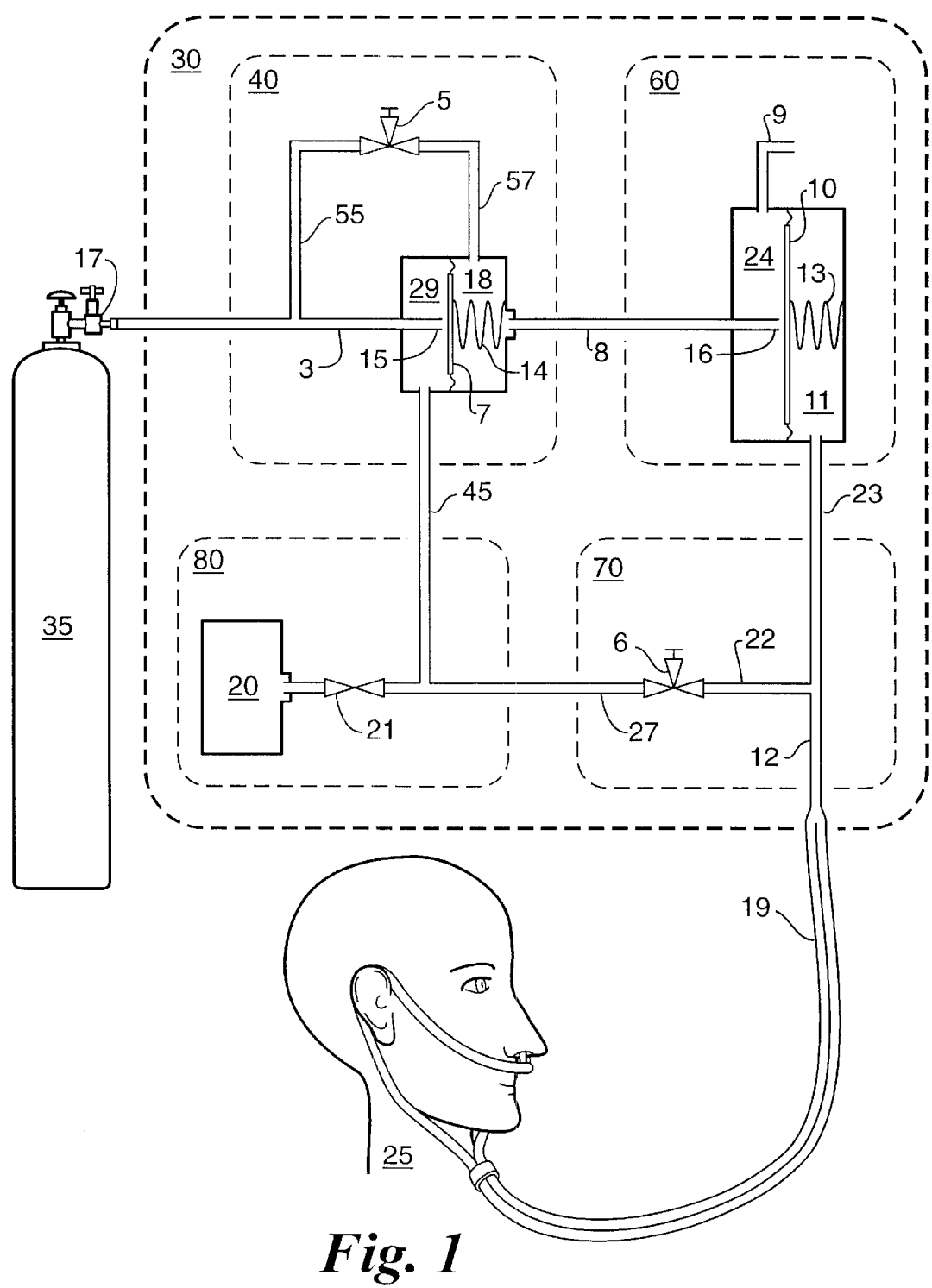
FIG. 1 is a schematic representation of the pneumatic oxygen conserving device.

Some oxygen delivery systems use a constant delivery of oxygen to a patient. The oxygen is supplied at an equal rate during the beginning and ending portions of a breath. When inhaling, the first portion of inspired oxygen goes to the lungs and the last portion of inspired oxygen remains in the patient's airway to be expelled during exhalation. The last portion of oxygen delivered is therefore wasted. To achieve an efficient use of oxygen, a device is required for applying oxygen only during the first portion of a patient's inspiratory cycle.

Breathing patterns in patients with lung disease have inspiratory times of approximately 0.5 to 1.7 seconds with an average of approximately 1 second. To be efficient, the pneumatic oxygen conserving device 30 should allow a specified volume of oxygen from oxygen tank 35 access to the patient 25 for about 0.5 seconds at the beginning of each breath, trailing off to a smaller volume thereafter for about another 0.5 seconds to avoid multiple pulse delivery.

The pneumatic oxygen conserving device 30 comprises a breath sensor portion 60 for sensing when the patient 25 begins inhaling, a gas delivery timer portion 40 for providing a timed delivery of oxygen to the patient during the first portion of inhalation, a variable flow rate portion 70 for adjusting the volume of oxygen delivered to the patient and tail volume delivery portion 80 for storing and delivering a volume of oxygen to the cannula after the initial inhalation to keep the pressure therein up so that an inhalation is not detected too early thus preventing pulsing of oxygen delivery. See patent WO 99/22795 entitled Oxygen Therapy Apparatus having a priority filing date of Nov. 4, 1997, which is attached hereto and incorporated herein by reference for a device which uses pulsing for oxygen delivery to the patient. The WO 99/22795 Oxygen Therapy Apparatus does not have a tail volume delivery portion 80 and therefore creates pulses of oxygen delivered to the patient as shown in FIGS. 5 and 6 of the WO 99/22795 patent.

The pneumatic oxygen conserving device 30 is connected to an oxygen source such as a bottle of oxygen 35 having a regulator 17 thereon for dispensing oxygen at a relatively low pressure such as from about 20 to about 100 psi for use by a patient 25. Although approximately 20 psi is preferred the Pneumatic Oxygen Conserving Device can be scaled to operate at any pressure.

The patient 25 has a cannula 19 for receiving oxygen from line 12. When the patient 25 begins to inhale a decrease in pressure draws a vacuum in cannula 19, line 12 and line 23, which is connected to the sensing chamber 11 in the breath sensor portion 60 of the pneumatic oxygen conserving device 30. The drop in pressure in the breath sensing chamber 11 draws the breath sensing diaphragm 10 away from breath sensing seat 16. The breath sensing diaphragm 10 may be spring loaded by spring 13 to bias the breath sensing diaphragm 10 in the closed position against breath sensing seat 16. With the breath sensing diaphragm 10 pulled back from the breath sensing seat 16, oxygen can flow from timing chamber 18, through connecting tube 8, to venting chamber 24, which is vented to the atmosphere by vent passage 9. The resulting drop in pressure in timing chamber 18 allows gas delivery diaphragm 7 to move away from gas delivery seat 15 allowing oxygen in delivery passage 3 to pass through gas delivery chamber 29 supplying oxygen to gas delivery tube 45 for access to the patient 25. The timing chamber 18 may have a delivery bias spring 14 for moving the gas delivery diaphragm 7 against gas delivery seat 15 to shut off the oxygen to the patient 25.

When gas delivery diaphragm 7 moves away from gas delivery seat 15, oxygen flows to the patient 25 for a limited time through the gas delivery chamber 29 of gas delivery timing portion 40. The gas pressure in delivery passage 3 and gas delivery chamber 29 tends to hold the gas delivery diaphragm 7 open, initially, due to the pressure applied to the diaphragm. Once flow commences to patient 25, from gas delivery chamber 29, pressure builds in cannula 19 and sensing chamber 11 causing sensing diaphragm 10 block sensing seat 16 with the aid of sensing biasing spring 13. This is countered by the gas delivery bias spring 14 and pressure building up from oxygen passing through tube 55, adjustable timing orifice 5 and, tube 57 into the timing chamber 18 to adjustably time the gas delivery through gas delivery seat 15.

The timing orifice 5 has an adjustable opening such that the timing of oxygen flowing through the gas delivery timer portion 40 is variable. The size of timing chamber 18 combined with the orifice size of timing orifice 5 varies the time the timing chamber 18 takes to fill up with gas to a pressure high enough for pushing gas delivery diaphragm 7 up against gas delivery seat 15 thus cutting off the oxygen flow through gas delivery chamber 29 to the patient 25.

To be most efficient, gas should be delivered in the first half of the patients' inspiratory cycle. Later delivery would not be effective, because late delivered gas never reaches the lungs. Breathing patterns in patients with lung disease create inspiratory times of approximately 0.5 to 1.7 seconds, with an average of approximately 1.0 second. To be efficient, the device should deliver most of the oxygen in 0.5 seconds or less. If this timing is used, most patients will still be inhaling when the gas delivery timer portion 40 finishes delivering gas.

Figure 2:
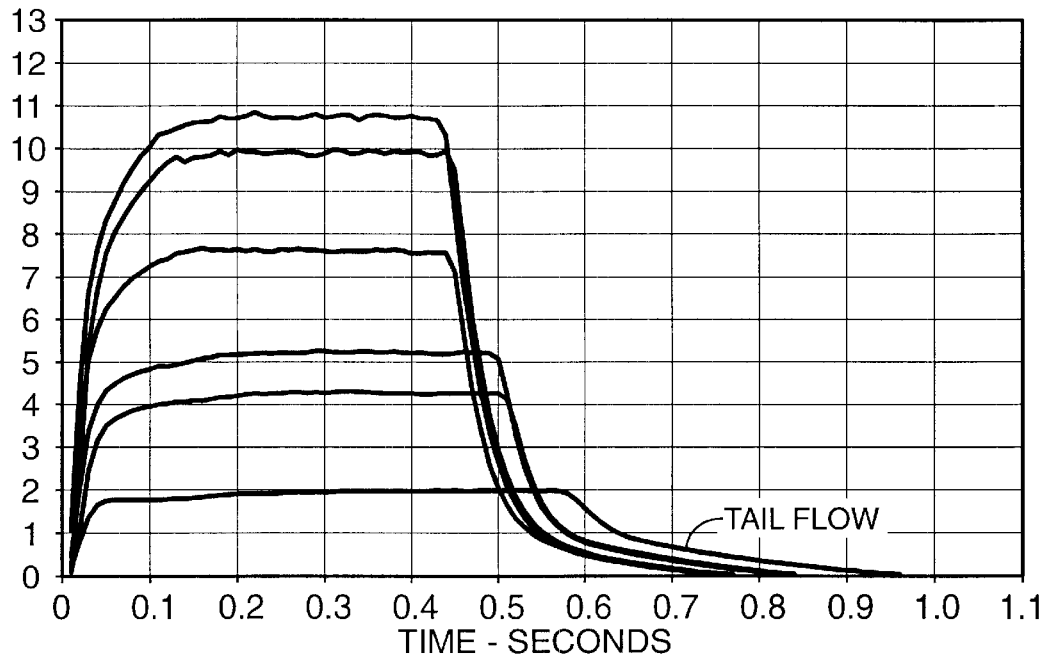
FIG. 2 is a graph of an oxygen flow delivery waveform.

The volume of gas and the shape of the pulse of gas delivered to the patient is controlled by the variable gas volume delivery portion 70 of the pneumatic oxygen conserving device 30. Typical oxygen delivery wave forms for the oxygen delivered through cannula 19 is shown in FIG. 2. The wave forms are adjustable for time and volume by use of timing orifice 5 and flow control valve 6. FIG. 2 shows volumes for different settings of flow control valve 6. The initial pulse has a sharp rise in flow followed by a steady flow for an adjustable period of time, from about 0.4 seconds to about 0.5 seconds. The volume of oxygen delivered then drops quickly to a low flow, and tails off slowly to zero, getting to zero at about 0.8 to 1.3 seconds.

By adjusting the flow control valve 6 the volume of oxygen passing into tube 22 can be controlled, thus the flow delivery waveform in FIG. 2 can be adjusted. Restricting the flow of oxygen through flow control valve 6 will decrease the volume of oxygen getting to the patient 25 through cannula 19.

In order to avoid a second, 'false' pulse of oxygen in the event that the patient's breathing effort is longer in duration than the oxygen delivery pulse, a 'tail' of oxygen delivery is added after the main pulse. This tail of low flow oxygen shown in FIG. 2 creates a back-pressure in the delivery cannula 19, shown in FIG. 3, keeping a positive pressure in sensing chamber 11 to avoid a false inhaling signal from being detected.

Figure 3:
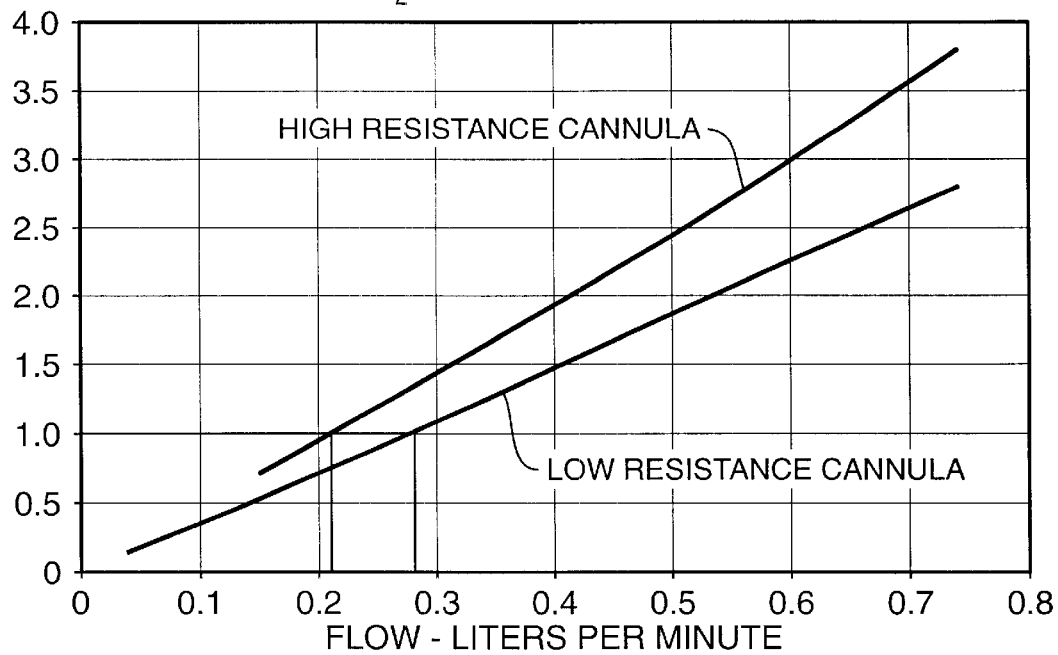
FIG. 3 is a graph of cannula back pressure.

Back-pressure measured in two typical cannulas (one with relatively high resistance to flow, and one with low resistance to flow) is shown in the graph of FIG. 3. Experience has shown that a typical patient, breathing normally through the nose will create about 1 cm H2O as a peak pressure (vacuum) in the cannula. This would imply that the presence of flows in the range of 0.2 to 0.3 lpm (with these cannulas) would create enough back pressure in the cannula that the sensing diaphragm could not be moved by the patient's inspiratory effort.

To accomplish this 'tail' flow, a reservoir 20 having a volume of about 2–5 mL is placed in between the gas delivery diaphragm 7 and the flow control orifice 6. An orifice 21 of approximately 0.010 inch diameter is placed at the inlet to reservoir 20. When the delivery diaphragm 7 is open, the inlet to reservoir 20 is pressurized to the regulator 17 pressure which is preferably approximately 20 psig. This causes the reservoir 20 volume to be 'filled' through the inlet orifice 21. When the delivery diaphragm 7 closes, the inlet orifice 21 to reservoir 20 volume is depressurized, so the gas bleeds back out of the inlet orifice 21, at a rate of approximately 1–2 lpm initially, decreasing as the gas pressure in reservoir 20 is depleted creating the "tail" flow in cannula 19.

This back pressure from the "tail" is only needed to prevent an new inhalation from being detected until the patient begins to exhale.

By varying the inlet orifice 21 and the volume of the reservoir 20, the profile of the tail can be tailored to optimize the effect. Ideally, the total time of the pulse delivery and the tail should be approximately 1.5 seconds. In this way, a patient with a breathing rate of 13 per minute (slow), and an inspiratory/expiratory time ratio of 1:2 would not get a double pulse, because their inspiratory time is approx. 1.5 second. On the other end of the scale, a patient breathing at 40 breaths per minute (quite fast) would still get a pulse on every breath, because their total breathing cycle is 1.5 seconds. In reality, the total time can be less than 1.5 second, because a patient's inspiratory flow decreases throughout their breath, so the time late in a long inspiratory time is not likely to create a double pulse, as there is less negative pressure generated in cannula 19.

Although the invention has been described herein as an oxygen delivery system any therapeutic gas delivered to the patient can be used in conjunction with the invention.

The sensing of the inhalation, the timing of the gas delivery and the control of the volume of gas can be detected and controlled by means other than those shown. The embodiment shown is for a pneumatic design.

Cannulas have been used to describe how oxygen is delivered to the patient however masks or other means for oxygen delivery to the patient may also be used with the invention.

Pistons or other movable barriers can replace the diaphragms in the embodiments shown.

Obviously, many modifications and variations of the present invention are possible in light of the above teachings. It is therefore to be understood that, within the scope of the appended claims, the invention may be practiced otherwise than as specifically described.

What is claimed is:

1. A pneumatic oxygen conserving device comprising:
   a breath sensor portion for detecting when a patient begins inhaling,
   a gas delivery timer portion connected to and triggered by the breath sensor portion, for opening a path for oxygen to flow from a source to a patient, for a controlled period of time during the patient's inhalation,
   a gas delivery portion, connected to the path for oxygen to flow to the patient, for controlling the gas presented to the patient during inhalation, and
   a tail flow delivery portion connected to the gas delivery portion for maintaining the pressure of gas delivered to the patient above a threshold indicating an inhalation while the patient is inhaling to avoid multiple pulses of oxygen being sent to the patient.

2. A pneumatic oxygen conserving device as in claim 1 wherein:
   the gas delivery timer portion has a variable controlled period of time for allowing oxygen flow to the patient.

3. A pneumatic oxygen conserving device as in claim 1 wherein:
   the gas delivery portion has a variable control for delivery of different volumes of gas to the patient.

4. A pneumatic oxygen conserving device as in claim 1 wherein:
   the breath sensor portion has a sensing chamber with a sensing diaphragm therein adjacent to and blocking a sensing seat when there is a positive pressure in the sensing chamber,
   a tube connected to the sensing chamber whereby the sensing diaphragm moves from the sensing seat under a negative pressure introduced to the sensing chamber through the tube, such that when the tube receives a negative pressure from a patient in association with the inhalation of the patient, the diaphragm moves from the sensing seat.

5. A pneumatic oxygen conserving device as in claim 4 wherein:
   the sensing diaphragm has a bias spring for urging the sensing diaphragm against the sensing seat.

6. A pneumatic oxygen conserving device as in claim 4 wherein:
   the breath sensor portion has a venting chamber bounded by the sensing diaphragm and containing the sensing seat, the venting chamber having a vent passage for venting gas to the atmosphere, such that when the sensing diaphragm moves from the sensing seat, gas entering the venting chamber can escape through the vent passage.

7. A pneumatic oxygen conserving device as in claim 6 wherein:
   the gas delivery timer portion has a timing chamber with a gas delivery diaphragm therein adjacent to and blocking a gas delivery seat when a combination of a spring pressure and the pressure in the timing chamber is applied,
   the timing chamber having a tube connecting the timing chamber to the sensing seat in the venting chamber of the breath sensor portion, such that the pressure in the timing chamber can be lowered thus moving the gas delivery diaphragm from the gas delivery seat when the sensing diaphragm is not blocking the sensing seat, and
   a tube for supplying gas under pressure connected to the timing chamber, such that gas entering the timing chamber can urge the gas delivery diaphragm against the gas delivery seat when it is not being vented though the venting chamber, thus blocking the gas delivery seat.

8. A pneumatic oxygen conserving device as in claim 7 wherein:
   the delivery diaphragm has a bias spring for urging the delivery diaphragm against the delivery seat.

9. A pneumatic oxygen conserving device as in claim 7 wherein:
   the gas delivery timer portion has a variable timing orifice connected to the tube for supplying gas to vary the gas delivery to the timing chamber such that the diaphragm can be urged against the delivery seat when gas enters the timing chamber over varying time periods.

10. A pneumatic oxygen conserving device as in claim 7 wherein:

the gas delivery timer portion has a gas delivery chamber bounded by the gas delivery diaphragm, the gas delivery seat connected to a source of gas, such that when the gas delivery diaphragm moves from the gas delivery seat, gas entering the gas delivery chamber can be delivered to a patient by passing through a gas delivery tube connected to the gas delivery chamber.

11. A pneumatic oxygen conserving device as in claim 10 wherein:

the gas delivery timer portion has a variable timing orifice connected to the tube for varying the gas delivery to the timing chamber such that the diaphragm can be urged against the delivery seat when gas enters the timing chamber at varying time periods to provide gas to the patient for varying periods of time.

12. A pneumatic oxygen conserving device as in claim 10 wherein:

the gas volume delivery portion has a flow control valve for restricting gas flow to the patient.

13. A pneumatic oxygen conserving device as in claim 12 wherein:

the gas volume delivery portion has a variable orifice to vary the volume of gas flow to the patient.

14. A pneumatic oxygen conserving device as in claim 11 wherein:

the gas volume delivery portion has a flow control valve for restricting gas flow to the patient.

15. A pneumatic oxygen conserving device as in claim 14 wherein:

the gas volume delivery portion has a variable orifice to vary the volume of gas flow to the patient.

16. A pneumatic oxygen conserving device as in claim 1 wherein:

a tail volume delivery portion has an orifice and reservoir to bleed the volume of gas from the reservoir creating a tail of gas pressure delivered to the patient.

17. A pneumatic oxygen conserving method comprising:

detecting when a patient begins to inhale, timing the delivery of gas to the patient beginning from after inhalation detection, delivering a flow of gas to the patient during the gas delivery time, tailing off of the flow of the gas delivered to the patient after the time for delivery of gas to the patient, keeping the back pressure up while the patient is still inhaling, to prevent multiple pulses of oxygen delivery.

* * * * *